United States Patent
Lewis et al.

(10) Patent No.: US 7,481,219 B2
(45) Date of Patent: Jan. 27, 2009

(54) MEDICINE DELIVERY INTERFACE SYSTEM

(75) Inventors: Charles Lewis, Carrabella, FL (US); Shara Hernandez, Davie, FL (US)

(73) Assignee: Mergenet Medical, Inc., Coconut Creek, FL (US)

( * ) Notice: Subject to any disclaimer, the term of this patent is extended or adjusted under 35 U.S.C. 154(b) by 555 days.

(21) Appl. No.: 11/108,690

(22) Filed: Apr. 19, 2005

(65) Prior Publication Data
US 2005/0279351 A1    Dec. 22, 2005

Related U.S. Application Data

(60) Provisional application No. 60/580,393, filed on Jun. 18, 2004.

(51) Int. Cl.
*A61M 16/00* (2006.01)
*A61M 15/08* (2006.01)
(52) U.S. Cl. .............................. 128/206.11; 128/207.18
(58) Field of Classification Search ............ 128/200.14, 128/200.21, 200.24, 204.12, 206.11, 206.28, 128/207.18, DIG. 24, 912, 204.28; 137/512.15
See application file for complete search history.

(56) References Cited

U.S. PATENT DOCUMENTS

| | | | | |
|---|---|---|---|---|
| 1,443,820 A | * | 1/1923 | Hudson | 128/202.13 |
| 2,185,997 A | * | 1/1940 | Heidbrink | 128/204.29 |
| 2,735,432 A | * | 2/1956 | Hudson | 128/207.18 |
| 3,836,000 A | * | 9/1974 | Jakubek | 210/104 |
| 3,915,173 A | * | 10/1975 | Brekke | 128/207.18 |
| 4,173,222 A | * | 11/1979 | Muetterties | 604/246 |
| 4,193,516 A | * | 3/1980 | Purdy et al. | 222/57 |
| 4,248,218 A | * | 2/1981 | Fischer | 128/204.18 |
| 4,278,082 A | * | 7/1981 | Blackmer | 128/207.18 |
| 4,278,110 A | * | 7/1981 | Price et al. | 137/805 |
| 4,327,741 A | * | 5/1982 | Watson et al. | 600/541 |
| 4,484,577 A | * | 11/1984 | Sackner et al. | 128/203.28 |
| 4,790,305 A | * | 12/1988 | Zoltan et al. | 128/200.23 |
| 4,867,153 A | * | 9/1989 | Lorenzen et al. | 128/205.12 |
| 4,915,105 A | * | 4/1990 | Lee | 128/205.27 |
| 4,919,128 A | * | 4/1990 | Kopala et al. | 128/207.18 |
| 4,967,742 A | * | 11/1990 | Theodorou | 128/202.13 |
| 5,195,515 A | * | 3/1993 | Levine | 128/203.26 |
| 5,222,491 A | * | 6/1993 | Thomas | 128/205.13 |
| 5,269,296 A | * | 12/1993 | Landis | 128/207.18 |
| 5,299,567 A | * | 4/1994 | Joye et al. | 128/204.28 |
| 5,401,262 A | * | 3/1995 | Karwoski et al. | 604/321 |
| 5,477,852 A | * | 12/1995 | Landis et al. | 128/207.18 |
| 5,495,848 A | * | 3/1996 | Aylsworth et al. | 128/207.18 |
| 5,572,994 A | * | 11/1996 | Smith | 128/207.18 |
| 5,687,715 A | * | 11/1997 | Landis et al. | 128/207.18 |
| 5,727,542 A | * | 3/1998 | King | 128/200.18 |
| 5,752,502 A | * | 5/1998 | King | 128/200.18 |
| 5,842,467 A | * | 12/1998 | Greco | 128/200.23 |
| 5,848,587 A | * | 12/1998 | King | 128/200.18 |

(Continued)

*Primary Examiner*—Justine R Yu
*Assistant Examiner*—Annette F Dixon
(74) *Attorney, Agent, or Firm*—Maier & Maier, PLLC

(57) ABSTRACT

Medicine delivery interface for delivery of therapeutic aerosols or gases, including at least one hollow body having at least one nasal aperture defined therein at least one nasal insert tube associated with each nasal aperture of the hollow body is capable of being inserted into a nostril. The interface also may include at least one exhaust aperture having at least one exhaust valve configured to exhaust exhaled gases and configured to block inflow of air through the exhaust aperture and at least one intake aperture.

31 Claims, 7 Drawing Sheets

U.S. PATENT DOCUMENTS

| | | | |
|---|---|---|---|
| 5,997,848 A * | 12/1999 | Patton et al. ................... 424/46 |
| 6,253,767 B1 * | 7/2001 | Mantz ................... 128/205.13 |
| 6,390,090 B1 * | 5/2002 | Piper ................... 128/203.28 |
| 6,478,026 B1 * | 11/2002 | Wood ................... 128/207.18 |
| 6,494,202 B2 * | 12/2002 | Farmer ................... 128/200.23 |
| 6,655,385 B1 * | 12/2003 | Curti et al. ............. 128/207.18 |
| 6,679,265 B2 * | 1/2004 | Strickland et al. ...... 128/207.18 |
| 6,763,832 B1 * | 7/2004 | Kirsch et al. ........... 128/207.18 |
| 6,863,069 B2 * | 3/2005 | Wood ................... 128/207.18 |
| 6,994,089 B2 * | 2/2006 | Wood ................... 128/207.18 |
| 7,047,974 B2 * | 5/2006 | Strickland et al. ...... 128/207.18 |
| 2002/0092527 A1 * | 7/2002 | Wood ................... 128/207.18 |
| 2003/0079749 A1 * | 5/2003 | Strickland et al. ...... 128/203.22 |
| 2004/0016432 A1 * | 1/2004 | Genger et al. .......... 128/204.18 |
| 2004/0045552 A1 * | 3/2004 | Curti et al. ............. 128/207.18 |
| 2004/0084046 A1 * | 5/2004 | Halperin ................. 128/201.13 |
| 2004/0134498 A1 * | 7/2004 | Strickland et al. ...... 128/207.18 |
| 2005/0042170 A1 * | 2/2005 | Jiang et al. ..................... 424/45 |
| 2005/0061326 A1 * | 3/2005 | Payne, Jr. .............. 128/206.11 |
| 2005/0066976 A1 * | 3/2005 | Wondka ................ 128/207.18 |
| 2005/0199242 A1 * | 9/2005 | Matula et al. .......... 128/207.13 |
| 2005/0205096 A1 * | 9/2005 | Matula et al. .......... 128/207.11 |
| 2006/0107958 A1 * | 5/2006 | Sleeper ................. 128/206.11 |
| 2006/0174887 A1 * | 8/2006 | Chandran et al. ...... 128/206.11 |
| 2007/0186930 A1 * | 8/2007 | Davidson et al. ....... 128/205.25 |
| 2007/0283957 A1 * | 12/2007 | Schobel (nee Bauer) et al. . 128/204.17 |
| 2008/0041393 A1 * | 2/2008 | Bracken ................ 128/207.18 |
| 2008/0051674 A1 * | 2/2008 | Davenport et al. .......... 600/561 |

* cited by examiner

MEDICINE DELIVERY INTERFACE SYSTEM

CLAIM TO PRIORITY

This application claims priority under 35 U.S.C. § 120 to Provisional U.S. Application Ser. No. 60/580,393, filed Jun. 18, 2004, the disclosure of which is incorporated by reference herein in its entirety.

BACKGROUND OF THE INVENTION

Exemplary embodiments of this invention improve and add utility to the nasal cannula devices sited herein. Exemplary embodiments of this invention may be used for any mammal, including horse, cattle, humans, and any other animal that breathes through a nasal cavity.

It is often desired to administer a medicine or one of a variety of gases to an animal, and in particular a mammal, such as a human, a dog or a horse, for pulmonary or nasal absorption. Direct application, such as by a spray or aerosol delivery device, or a dry powder delivery device, is difficult due to movements of the animal and may lead to improper application or delivery of the medicine as well as discomfort of the subject. To enable such application of medicines in the conventional art, an elongated, generally cup-shaped "mask" is often provided, having a relatively large open base end for fitment over a subject's nostril or muzzle and having a medicament administration port opposite that base end. Typically the mask is made out of a semi-rigid material (e.g., sheet polycarbonate) and is provided in various sizes for use with different sized animals. The mask, however, is not easily adaptable or adjustable to fit over the nostrils or muzzle of a range of sizes of one type of animal or different sizes of different types animals or humans. This requires a variety of different size masks to be available in order to treat different animals or humans.

In use in the conventional art, an appropriate sized mask must therefore be selected. The open base end of the mask is then positioned over the subject's nostril or muzzle, typically only sealing to the nose or muzzle of the animal or human through friction between the mask and the animal or human. The size of the open end is such that only a rough seal is established between the open end of the mask and the animal's or human's nostril or muzzle. When the mask is so positioned, medicine or gas is delivered through an administrative port, for example by spray, aerosol delivery device, or dry powder medicine delivery device, either breath-activated or user-driven. As the animal or human breathes, the medicine is drawn into one (or both) nostril(s), or in the mouth and into the lungs or the nasal passages. However, due to the design and structure of these masks, medicine or gas may not be properly administered to the mouth or nostrils of the animals or humans as there is a significant distance between the administrative port and the mouth or nostrils of the animal. Additionally, due to the lack of a seal between the mask and the animal or human, medicine or gas may escape from the mask, preventing the animal from receiving the medicinal benefits.

There are further inconveniences and problems associated with the conventional art masks. More particularly, because of the semi-rigid structure of such masks, the masks are bulky and take up significant volume when carried around by a veterinarian, or other provider. A further problem with these masks is the discomfort caused to the animal or human. Because these masks cover the entire nose and mouth of the animal or human, the animal or human is unable to use its mouth or eat when the mask is being worn. This may cause animals in particular to try to dislodge the mask in an effort to regain the use of their mouth. The dislodging of the mask may further lead to damaging the mask, rendering it incapable of repeated use. A further problem with these masks is their bulk, which may cause discomfort when an animal or human tries to sleep.

None of the above inventions and patents, taken either singly or in combination, is seen to describe the instant invention as claimed.

SUMMARY OF THE INVENTION

An interface for delivery of therapeutic aerosols or gases, including at least one hollow body having at least one nasal aperture defined therein. It also has at least one nasal insert tube associated with each nasal aperture of said hollow body is capable of being inserted into a nostril. The interface also includes at least one exhaust aperture having at least one exhaust valve configured to exhaust exhaled gases and configured to block inflow of air through the exhaust aperture and at least one intake aperture.

In another exemplary embodiment of the present invention, the interface for delivery of therapeutic aerosols or gases may include a hollow, arcuate nasal cannula having a semi-cylindrical shape. The nasal cannula may further include nasal inserts and expiration ports, as well tubes used for coupling the nasal cannula to ventilator supply tubes. The nasal inserts may provide a seal between the inserts and the nares of a user. Further, the nasal interface may have at least one connector tube coupled to the nasal cannula, at least one reservoir bag coupled to the at least one connector tube and at least one nebulizer coupled to the reservoir bag.

In yet another exemplary embodiment, a method for delivery of therapeutic aerosols or gases is shown comprising providing at least one hollow body having at least one nasal aperture defined therein. Then inserting at least one nasal insert tube associated with each nasal aperture of said hollow body into a nostril. Next, delivery of at least one of therapeutic mists, vapors, aerosols and gases to the nasal interface and expelling at least one of exhaled air through at least one exhaust aperture having at least one exhaust valve.

In another exemplary embodiment, an interface for delivery of therapeutic aerosols or gases, comprising means for delivery of aerosols through at least one hollow body having at least one nasal aperture defined therein; means for sealing at least one nasal insert tube associated with each nasal aperture of said hollow body with a nostril; means for exhausting exhaled gas; means for blocking inflow of air through the means for exhausting exhaled gas; and means for intake of at least one of therapeutic aerosols or gases.

BRIEF DESCRIPTION OF THE DRAWINGS

Advantages of embodiments of the present invention will be apparent from the following detailed description of the exemplary embodiments thereof, which description should be considered in conjunction with the accompanying drawings in which.

DETAILED DESCRIPTION

Figure 1A:
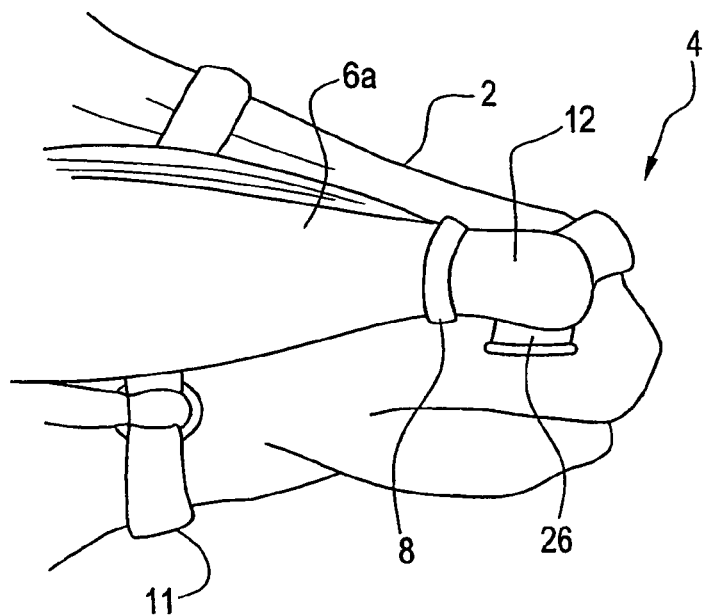
FIG. 1A shows a perspective view of an exemplary embodiment of a nasal insert.
Figure 1B:
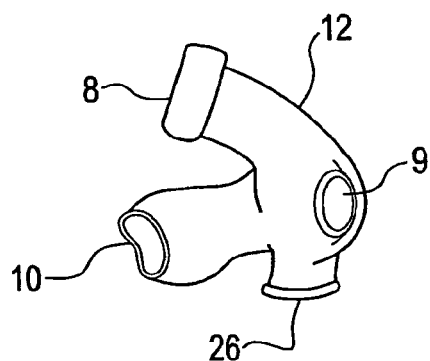
FIG. 1B shows another perspective view of an exemplary embodiment of a nasal insert.
Figure 2:
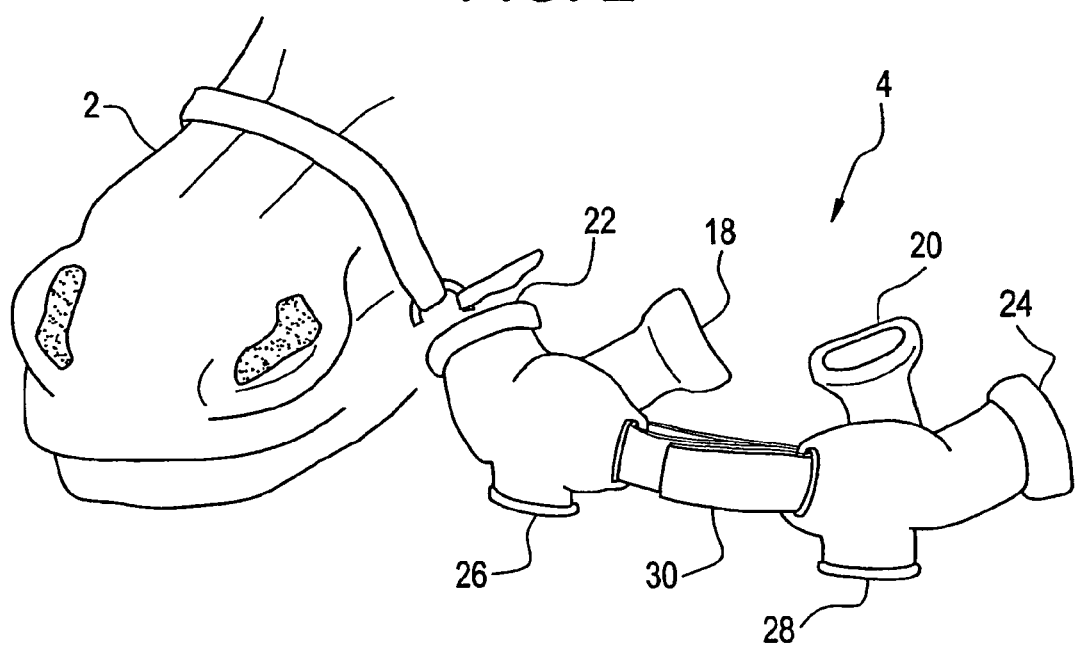
FIG. 2 shows a perspective view of an exemplary embodiment of a nasal insert.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description, discussion of several terms used herein follows.

Referring now to the drawings, wherein like reference numerals designate identical or corresponding parts throughout the several views.

Generally referring to FIGS. 1A-10B, a single or multiple intranasal device and system for self sealing airways for delivery of aerosolized or gaseous medications is discussed. This device will allow for any medicinal or non-medicinal gaseous or aerosolized delivery. For example, the interface system may optionally be configured to deliver at least one of oxygen, aesthetic gases or aerosols, for example, to treat asthma or lung infections as non-limiting examples. The interface system may optionally be configured to deliver any gases or aerosols, for medicinal treatment using aerosol delivery.

FIG. 1A-1B illustrate exemplary embodiments of the present invention. The face and, for exemplary purposes, snout of horse 2 is shown with intranasal device 4 attached. In other exemplary embodiments, the face or snout of another species of mammal may be used with the present invention. Intranasal device 4 is fitted to the snout 2 optionally connecting to reservoir bag 6*a* and harness 11. The intranasal device 4 may include connector 8, which may connect to an air or medication source, and nasal insert 10, through which air, anesthetic, oxygen other gases or medication can flow into the nares of the horse.

Additionally, the intranasal device 4 includes a body 12 and expiration port 26, which allows undesired expiration air or gases to escape the intranasal device 4. Additionally, expiration port 26 may have a one way valve, such as, for example, a flap valve 72 (see FIG. 8A-8F) that places resistance on inward air flow. A flap or one-way valve 72 may allow inward air to enter through connector 8. Additionally, the valve 72 may optionally block any inward air flow. Alternatively, the valve 72 may fail if sufficient force is present, such as if sufficient force is present, such as might occur if the inlet ports were blocked. Further, reservoir bag 6*a* may be connected to intranasal device 4, optionally using the connector 8 which allows the reservoir bag 6*a* to be coupled to intranasal device for the administration of air or medication to the nares of a mammal or animal.

FIG. 2 illustrates another exemplary embodiment of the present invention. Snout 2 is shown to illustrate one possible fitment of intranasal device 4. In this exemplary embodiment, intranasal device has nasal inserts 18 and 20 which may be inserted into the nares of snout 2. The nasal inserts 18 and 20 could be made in various sizes and shapes to fit different individuals and species. Also, there may be a flange formed as a bead disposed about the distal tip end of each said nasal insert. The flange may be adapted for forming a seal against a naris of mammal's nose. The flange may also be configured as a skirt member configured to aid in sealing the insert tube. Intranasal device further has coupling sections 22 and 24 that may be used to connect intranasal device 4 to a gas or aerosol delivery tube. Additionally, expiration ports 26 and 28 are disposed on the lower portion of intranasal device for the elimination of undesired air or exhaust gases. Adjustable connector 30 is disposed between the left and right portions of intranasal device 4. Connector 30 may allow for the adjustment of the distance between nasal inserts 18 and 20. The adjustment of intranasal device 4 allows for the fitment of a wide variety of sizes and shapes of snout 2 or, in other exemplary embodiments of the present invention, the fitment of intranasal device to a variety of different species of mammals. Further, adjustable connector 30 may include an adjustable strap or connector to aid in getting the proper fit to the animal. In one exemplary embodiment, Velcro™ or any of a variety of adjustable connectors may be used to make the adjustable connector 30. Additionally, in another embodiment of the invention, loops or eyes may be placed on various portions of this device in order to strap it to the user, or optionally to attach it to a halter or harness on a mammal. Further, connector 9 may be used to connect the internasal device 4 to another internal device 4.

In another embodiment of the present invention, the interface may be used for long periods of time, for example, many hours or days. Because there is not a pressure contact seal provided by the nasal inserts, tissue damage associated with other medicine delivery interfaces and masks that have such pressure contacts may be avoided. An extended distribution period for medication or therapeutic gases allows for high volume medication delivery, which may be given at a low rate per minute. Additionally, the ability of the device to be worn for long periods of time allows for a wider array of medications to be delivered, and allows for medications that require milligram doses rather than microgram doses to be delivered through the respiratory tract. For example, suitable antibiotics may be delivered to the lungs through this device, in part as a result of long time the interface may be worn.

In another exemplary embodiment the interface may also be used to treat other respiratory conditions or be configured to deliver oxygen or other medicinal gas treatment. Likewise, the device may be configured for pressurized delivery of medication or air. The ventilation interface may include a pair of nasal inserts that may be configured to provide a seal between the interface and the nares. The distal tip end 10 may be configured with a skirt, double skirt, flange or substantially oval distal to aid in sealing in the nares. The interface 12 may have at least one base end adapted for connection to a ventilator for air flow and at least one distal tip end 10. The interface may include at least one adjustable connector disposed on the ventilation interface that allows the device to fit a variety of patients.

Figure 3:
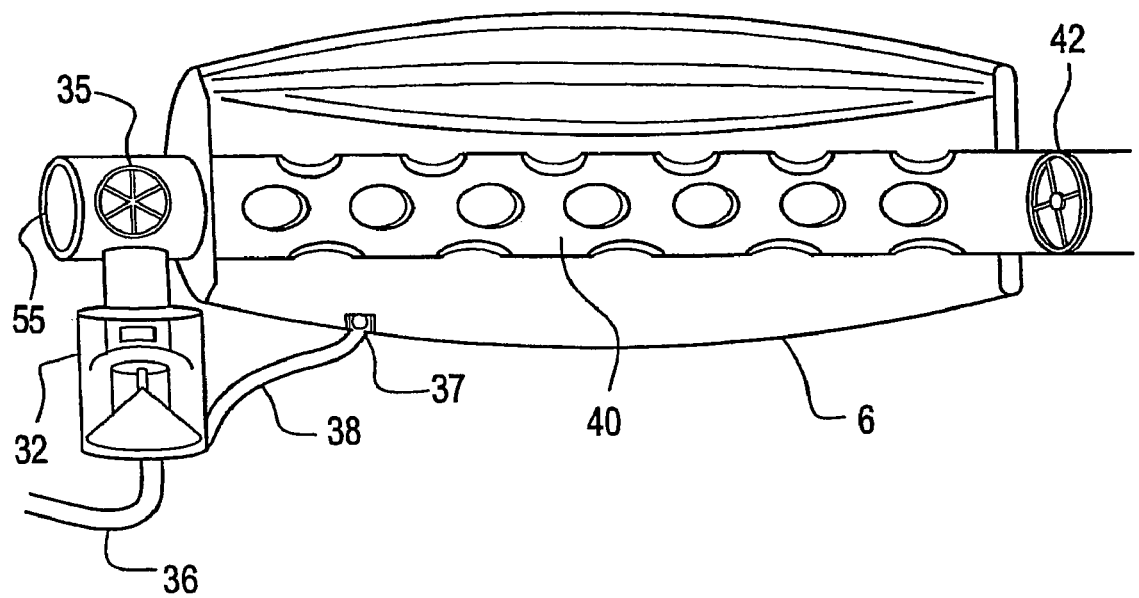
FIG. 3 shows a cross-sectional view of an exemplary embodiment of a reservoir chamber associated with a nebulizer.

FIG. 3 illustrates cross-sectional view of an exemplary embodiment of a nebulizer with a reservoir 6a for nebulized aerosols with an expandable outer wall, and a rigid center pipe that prevents collapse of the air delivery route. In one exemplary embodiment, nebulizer 32, may be a jet nebulizer or any of a variety of nebulizers, may be used. Nebulizer 32 may act to run continuously and deliver medication, and using a reservoir may help decrease the release of medication or gas which might contaminate the ambient air.

The nebulizer 32 also acts to increase the amount of medication delivered during each respiratory cycle. Nebulizer 32 can be disposed on an upper portion or end portion of reservoir bag 6a, depending on the fitment to the face or snout of the mammal. Reservoir bag 6a may be a bellows-shaped expandable envelope. The nebulizer 32 may allow for the combination of air, oxygen, anesthetic or other gas or gas mixtures. Further, the use of a reservoir 6a with the nebulizer 32 may also act to increase the amount of medication delivered.

In one exemplary embodiment, the medication may be administered to the user of the device for the treatment of asthma, pneumonia, bronchitis or other respiratory diseases. Asthma, for example, may be treated with microgram doses of medication through an intranasal device that is worn. Additionally, because the intranasal device may be worn for long periods of time, for example, several hours, treatment utilizing larger amounts of medication may be performed that deliver anesthetic gases, antivirals or antibiotics directly to the target tissues of the user of the device.

Nebulizer 32 may produce a fine mist that can be administered to the horse or any other of a variety of mammals nasally. Single or multiple nebulizers may be designed to attach close to the airway, or be part of the airway device to improve performance, as aerosolized particles coalesce and be less effective in entering the desired point of treatment when the nebulized mist is further from the point of delivery.

Nebulizer 32 may further incorporate a switching device or a reservoir may be used with at least one of a nebulizer or a dose inhaler (MDI) to decrease medication wastage, better control dosing, and to decrease air contamination. In another embodiment, a switching, device can be used to control air or medication flow, decrease medication wastage, better control dosing and decrease air contamination through an opening and closing action. A switching device may also be used without a reservoir. When the switching device is in a closed position, air or medication may flow through tubing 36 and continue into reservoir bag 6a. When the switching device is in the open position, air or medication may flow through tubing 36 and into nebulizer 32, and then into reservoir bag 6a.

In another embodiment of the invention, tubing 36 may be a pressurized air tube, used, for example, with a jet nebulizer. Additionally, return tube 38 may be disposed in such a manner as it may act as a return tube 38 for aerosols that fall out of suspension. The return tube may be connected to the reservoir 6 at the float valve 37 which may be configured to open only when fluid has collected in the reservoir bag 6a. The float valve 37 may allow drainage of condensate in the reservoir bag 6a. If there is no liquid condensate present, the float valve 37 should remain closed so that aerosol and gas is not drawn back into the nebulizer 32 by negative pressure of the venturi effect in the nebulizer 32. If liquid condensate is present the small float above the opening and will allow passage of the liquid to the nebulizer 32 reservoir bag 6a.

In another embodiment, this device may incorporate an on-demand switching nebulizer. One method for this is a pressure sensitive switch which activates the nebulizer 32. An on-demand nebulizer would conserve medication, decrease medication release into the environment, and give more controllable dosing of medication. Other activation mechanisms may use flow detection, valves, or regulators.

In another embodiment of the invention, nebulizer 32 may be a vibrating mesh nebulizer, or similar type of electronic nebulizer, which allows use in a variety of positions. This would allow the nebulizer to be in close proximity to the nares, which may improve efficacy and work in concert with provisions above.

The nebulizer 32 may be designed to be used for long time periods, allowing for long dosing times and permitting large dose delivery, even at low flow rates. While traditional nebulizers are designed for short dosing periods in minutes, this device can be used for hours, perhaps for days.

In further exemplary embodiment with respect to FIG. 3, nebulizer 32 can be used to improve performance of the airway device, as aerosolized particle may coalesce and be less effective in entering the desired point of treatment. For example, 1.5 to 3.5 micron particle may be best to enter the bronchiole. Alternatively, 5-25 micron particles, or a variety of different sized particles, may be used depending on the size of the airway or any size that may effectively enter the bronchiole of the user. As particles coalesce, they become larger and do not enter these small airways. Those skilled in the art may appreciate any other suitable sized particles may be used depending upon the various system parameters including, for example, cannula size, air flow rate, or size of medicated mammal.

In another embodiment of the invention, a humidifier may be used interchangeably with nebulizer 32 or elsewhere ported into the system. In this embodiment, humidified air may be delivered through the system to provide a therapeutic effect on the user.

FIG. 3 also includes ventilated support tube 40, which may prevent collapse of air delivery route. Ventilated support tube 40 is disposed on the interior of reservoir bag 6a and allows for the passage of air or medication through reservoir bag 6a. Ventilated support tube 40 may have a rigid or semi-rigid structure which may prevent it from collapsing with outside pressure, such as if the mammal using the device where to lean against a barrier. Also, one-way exit valve 42 may be disposed at a distal end of Ventilated support tube 40. Alternatively, an air intake valve 35 may also be positioned in close proximity to the nebulizer 32 and nebulizer connection module 55 to provide medication and air delivery if there is failure in the gas or air flow. A one-way exit valve 42 can be used to control direction of air and medication flow through the device. In one embodiment of the present invention, one-way exit valve 42 may be used to prevent the backflow of gases into nebulizer 32.

Figure 4:
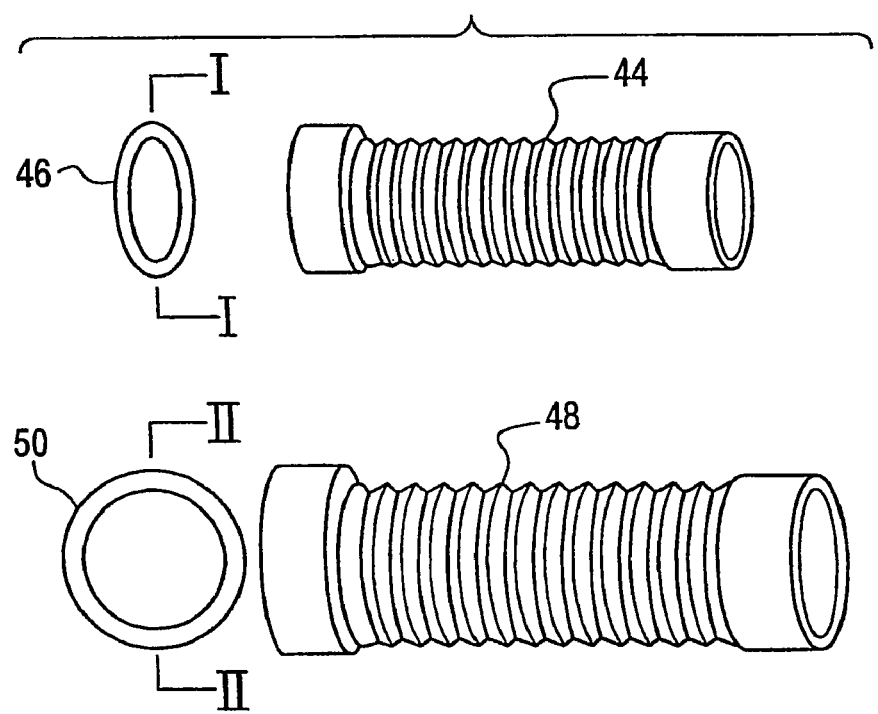
FIG. 4 shows an exemplary embodiment of a connector tube.

FIG. 4 shows an exploded view of a connector tube in another exemplary embodiment of the invention. Connector tube 44 may be fitted to the nasal interface system in a location after one-way exit valve 42. Connector tube 44 features a tube structure that is adjustable and flexible and may communicate pressure between the nostrils of a user. In one embodiment of the invention, connector tube 44 may be used interchangeably with adjustable connector 30 provided the intranasal device 4 is configured with holes 9 to receive a connector tube 44. In alternative exemplary embodiments of the invention, a connector tube 44/48 may be used in place of the connector 30. The flexible tubing allows the nasal interface system to be worn on a variety of sizes of mammals, as the tubing can expand and contract to fit a variety of facial sizes and structures. The tubular structure would allow communication of airflow, pressure and medication. These connectors could be made from a multitude of sized pieces, of which an appropriate size could be selected for use, and/or they may be adjustable. An adjustable tubular structure could be made in the manner of the telescopic portion of a soda straw. Tube 44 in may optionally be flattened, oval or collapsed.

A cross sectional view I-I of the connector tube 44 is shown in FIG. 4. The outer perimeter 46 of the tube 44 is shown in a substantially oval configuration. The tube 44 may be any of a variety of materials and provide an air tight seal between connector tube 44 and other portions of the nasal interface device 4. Additionally, cross section I-I of 44 may be any of an oval, elliptical or circular shape. An O-ring (not shown) may also be used to connect the tube 44 to the interface.

Connector tube 48 is a larger connector tube, demonstrating that different size tubes may be used for mammals of different sizes. Connector tube 48 also has adjustable and flexible tubing, further allowing fitment to a larger variety of mammals. For example, the connector tube 44 may be oval or flattened to stretch across the nose of large mammals. Connector tube 48 may, in another embodiment of the invention, be used interchangeably with adjustable connector 30. Additionally, a cross sectional view II-II showing the substantially circular outer perimeter of 50 of tube 48 is shown in FIG. 4. In another exemplary embodiment, connector tubes 44 or 48, as well as a variety of other size connector tubes may be used interchangeably in the nasal ventilation device. An O-ring (not shown) may also be used to connect the tube 48 to the interface.

Figure 5:
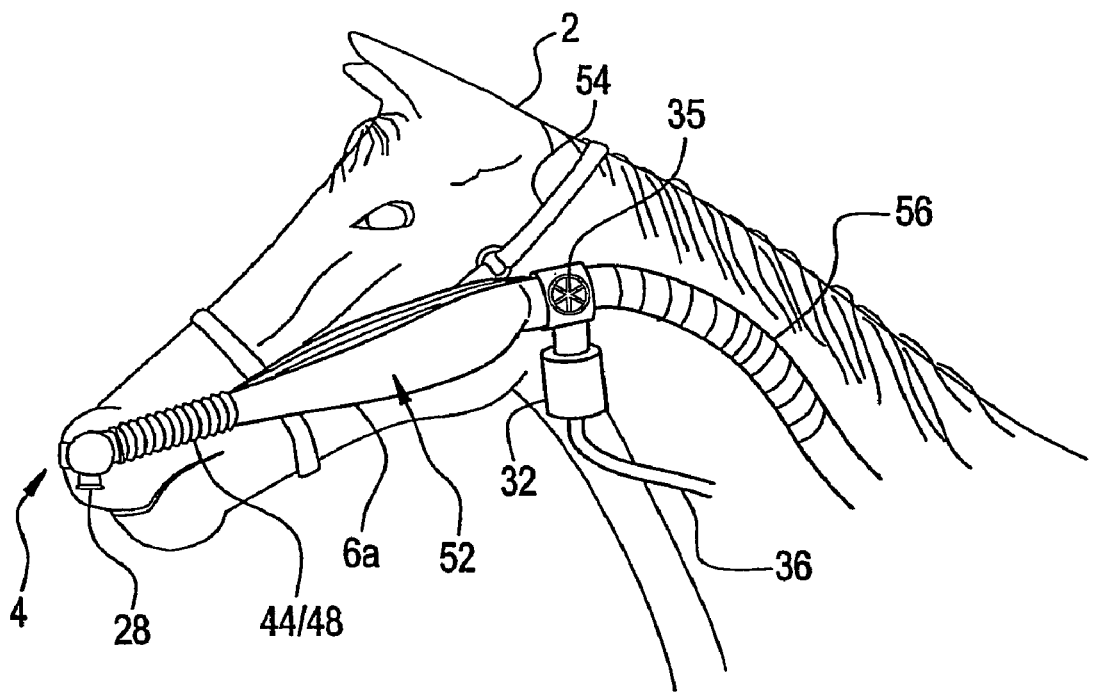
FIG. 5 shows an exemplary embodiment of a medicine delivery interface system.

FIG. 5 shows another exemplary embodiment of a medicine delivery interface system. In FIG. 5 the nasal interface device 52 is shown as being worn by a horse 2. The nasal interface device 52 may be held in place with harness 54, which secures the device on the horse's or, optionally any mammal's, head or snout. In one embodiment of the invention, tubing 36 or tubing 56 may feed air, oxygen, other gases or an aerosolized medication. In another embodiment, tubing 36 and tubing 56 may feed gases directly to the nasal interface device without utilizing a reservoir bag. In different embodiment of the invention, tubing 36 and tubing 56 may feed air, oxygen, other gases or an aerosolized medication to reservoir. For example, a reservoir 6a may be may be used when warm air, moisturized air or humidified air is being fed through the intranasal device to reduce the potential of gas or liquid escaping from the device.

In another embodiment of the invention, tubing 36 and tubing 56 may deliver humidified air to the device. In this embodiment nebulizer 32 could be interchanged with a humidifier or, alternatively, a humidifier could be disposed in a variety of locations on the medicine delivery interface system.

In yet another embodiment of the invention, tubing 36 could be a water or medication supply tube. In this embodiment, tubing 36 may have single or multiple channel tubing for the supply of air, gases, pressure or medication. Tubing 36 may also house wires for delivery of electrical power to, for example, an electrically operated nebulizer or humidifier.

In another embodiment, tubing 56 may have a double wall chamber that allows warm gases, humidified air or medication to be delivered through the tubing. In this embodiment, the warm gases, humidified air or medication traveling through double-walled tubing 56 would be more insulated from ambient conditions and prevent the gases, air or medication from being cooled by those ambient conditions.

Reservoir bag 6a or 6b is connectably attached to connector tube 44 or 48, or any other of a variety of different size connector tubes, depending on the size and desired fitment to the horse or other mammal. Connector tube 44 or 48 may then be connected to intranasal device 4. The nasal inserts 18 and 20 (not pictured) of intranasal device 4 are inserted into the nares of horse 2. Additionally, expiration port 28 is shown as being optionally positioned in a downwards angle.

Figure 6:
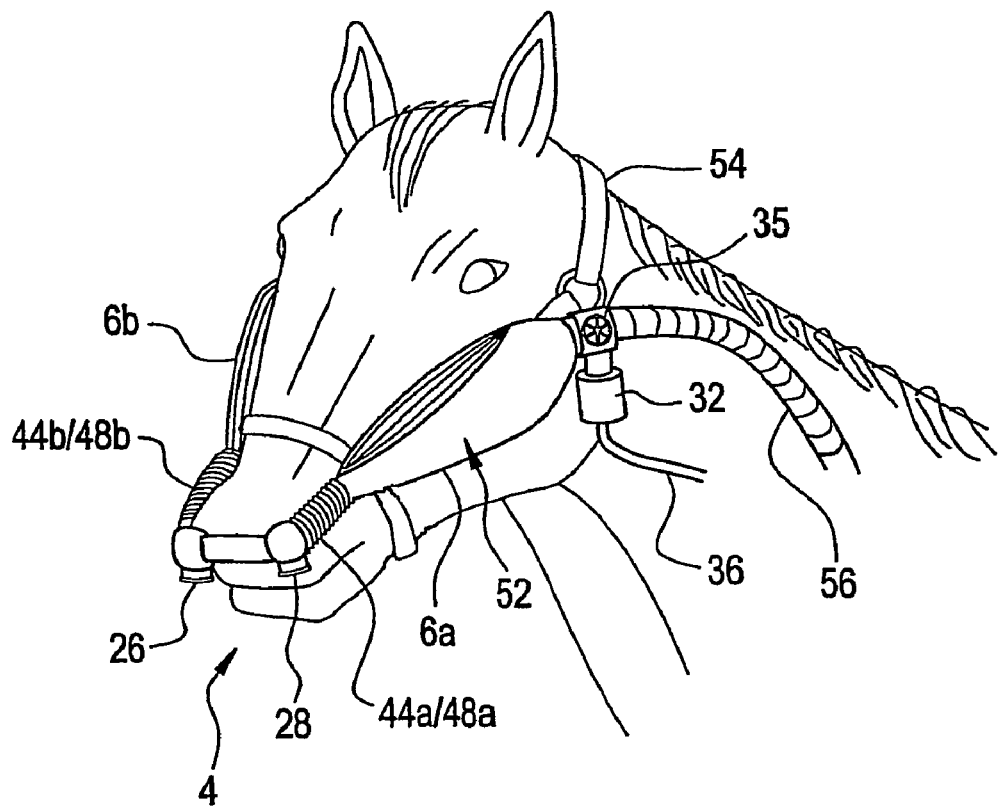
FIG. 6 shows an exemplary embodiment of a medicine delivery interface system.

FIG. 6 shows another exemplary view and embodiment of nasal interface system 52. In this figure an optional second reservoir bag 6b is shown opposite first reservoir bag 6a, as a single or multiplicity of volume reservoirs may be used for gases and medication. Reservoir bag 6b may have its own nebulizer and other associated connecting and delivery tubes. Also, the device may have one or more gas and medication inlet ports, such that a gas and medication inlet port could be associated with each reservoir bag 6a and 6b. Reservoir bag 6b connects to connector tube 44b or 48b in a similar manner that reservoir bag 6a connects to connector tube 44a or 48a. Further, connector tube 44b or 48b connects to intranasal device 4 in a similar manner that connector tube 44a or 48a connects to intranasal device 4. Further, expiration ports 26 and 28 are shown as being optionally positioned in a downward angle.

In a further exemplary embodiment, connector tubes 44a and 44b and 48a and 48b may be connected directly to the air intake valve(s) (e.g. air intake valve 35). In this embodiment, reservoir bags 6a and 6b could be replaced by any of a variety of different types of tubing.

In another exemplary embodiment, the expiration ports 26 and 28 for large animals for exhalation may be pointed downwards to avoid, for example, a blast of mucous and/or airflow directed at animal caretakers. In another embodiment, one-way exhalation valves could be placed across from the nostrils to exit breath and to reduce the likelihood of ejection of the device with snorting or sneezing of the animal.

Additionally, as shown in FIG. 6, the device may be configured to be used and allow the user to eat and drink. From FIG. 6 it is demonstrated that the horse or, optionally, any other of a variety of mammals, would retain full function and availability of its mouth, allowing it to eat and drink.

Figure 7:
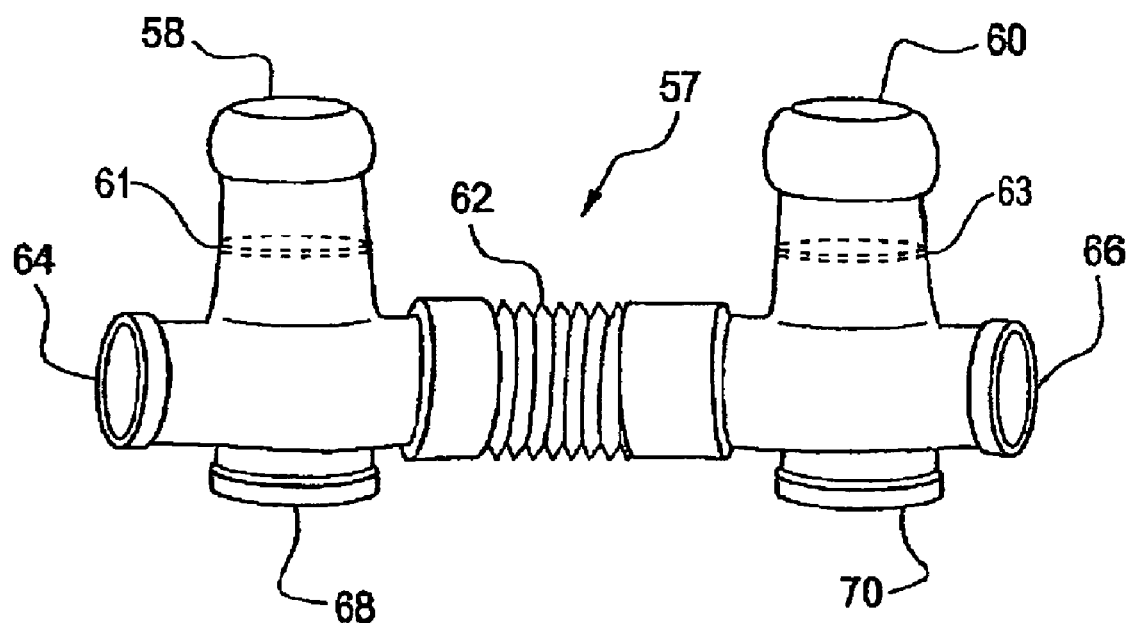
FIG. 7 shows another exemplary embodiment of a medicine delivery interface system.

FIG. 7 shows another exemplary embodiment of a nasal interface system. Nasal inserts 58 and 60 are disposed on the upper portion of the intranasal device 57, and may be formed and shaped in a variety of sizes, in order to fit a variety of mammals or users. Filters 61 and 63 may be coupled within nasal inserts 58 and 60, respectively, such that filters 61 and 63 are positioned substantially proximate to an intake aperture of nasal inserts 58 and 60, respectively. Connector 62 is a sizable connector, similar to those found on a flexible soda straw. Additionally connector 62 may have a variety of different sizes or selectable parts so that the device can adapt to animals having different distances between their nostrils.

FIG. 7 further includes connecting ports 64 and 66 that are disposed on opposite ends of intranasal device 57 and allow the device to connect to other portions of the previously described nasal interface device. These openings may optionally include one-way inlet valves that would increase effective air flow and decrease dead air space and waste. Additionally, valves 64 and 66 may be connected to reservoir bag 6 that may incorporate a nebulizer to decrease waste and air contamination, as well as control dosing of medication.

Additionally, FIG. 7 shows expiration ports 68 and 70 are disposed on the lower portion of intranasal device 57. The expiration ports may optionally be one-way valves that assist in cycling out exhaled gases and, additionally, prevent the ejection of the intranasal device 57 from the animal, for example, after sneezing. Additionally, in FIG. 7, loops or eyes may be incorporated to allow the device to attach more securely to straps or a harness mounted on a mammal or user's head.

In another exemplary embodiment of the present invention, a valve may be disposed in one of the ports on the interface device. In one exemplary embodiment, expiration ports 68 and 70 may include an exit valve 72. In another exemplary embodiment, a valve 72 may be disposed on connecting ports 64 and 66. Exemplary diagrams of the exit valves 72 that may be disposed in the expiration ports or the connecting ports are shown in FIGS. 8A-F.

Figure 8A:
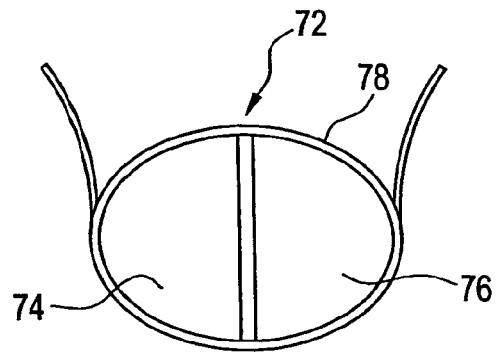
FIG. 8A shows a bottom view an exemplary embodiment of a one way flap valve in the closed position.
Figure 8B:
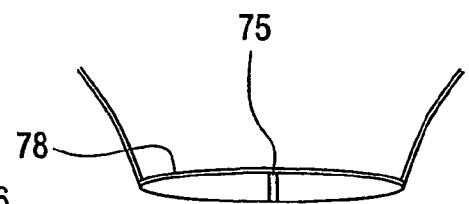
FIG. 8B shows a side view of an exemplary embodiment of a one way flap valve in the closed position.
Figure 8C:
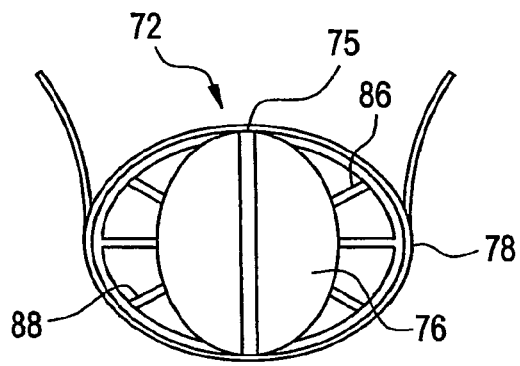
FIG. 8C shows a bottom view exemplary embodiment of a one way flap valve in the open position.
Figure 8D:
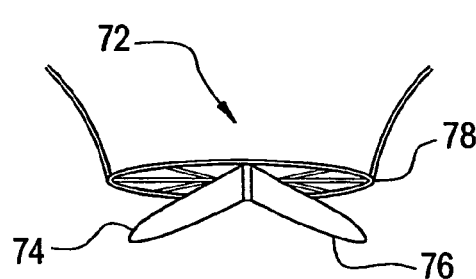
FIG. 8D shows a side view exemplary embodiment of a one way flap valve in the closed position.

FIGS. 8A and 8B show a bottom view of valve 72 in a closed position. When in a closed position, flexible membranes 74 and 76 are in connection with cross member 75 and tension ring 78, thus creating a seal and preventing inward air or any other fluid movement. FIGS. 8C and 8D show a bottom view of valve 72 in an open position. When valve 72 is open, flexible membranes 74 and 76 are separated from tension ring 78, thus allowing outward air or any fluid movement. FIG. 8D shows a rotated side view of open valve 72. In this view, it is clear that air or any other gas may flow through valve 72 and past flexible membranes 74 and 76.

Figure 8E:
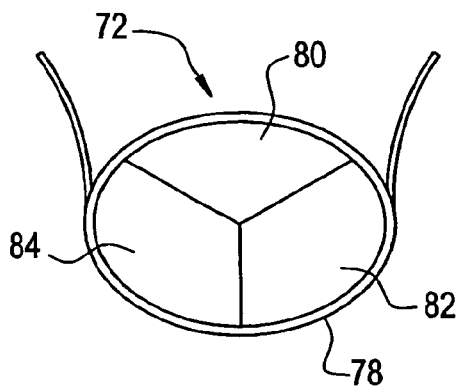
FIG. 8E shows a bottom view exemplary embodiment of a one way flap valve in the closed position.
Figure 8F:
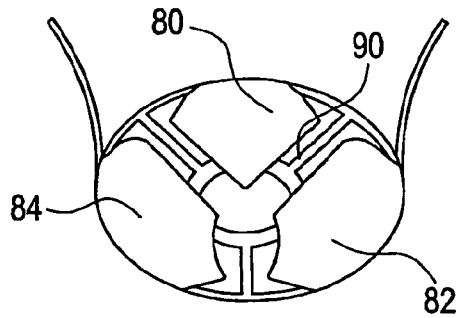
FIG. 8F shows a bottom view exemplary embodiment of a one way flap valve in a partially open position.

In another exemplary embodiment, FIGS. 8E and 8F show a bottom view of valve 72 in a closed position. When in a closed position, flexible membranes 80, 82 and 84 are in connection with central support member 90 and tension ring 78, thus creating a seal and preventing inward air or any other fluid movement. The central support member 90 may be configured to allow retrograde flow under sufficient negative pressure situations, for example, if the primary airway is impeded. FIG. 8F shows a bottom view of valve 72 in an open position. When valve 72 is open, flexible membranes 80, 82 and 84 are separated from the tension ring 78, thus allowing outward air or any fluid movement. Additionally, FIG. 8C shows additional support members 86 and 88, which provide additional support to valve 72 and act in coordination with cross member 75. FIG. 8F shows a bottom view of open valve 72. In this view, it is clear that air or any other gas may flow through valve 72 and past flexible membranes 80, 82 and 84.

Figure 9:
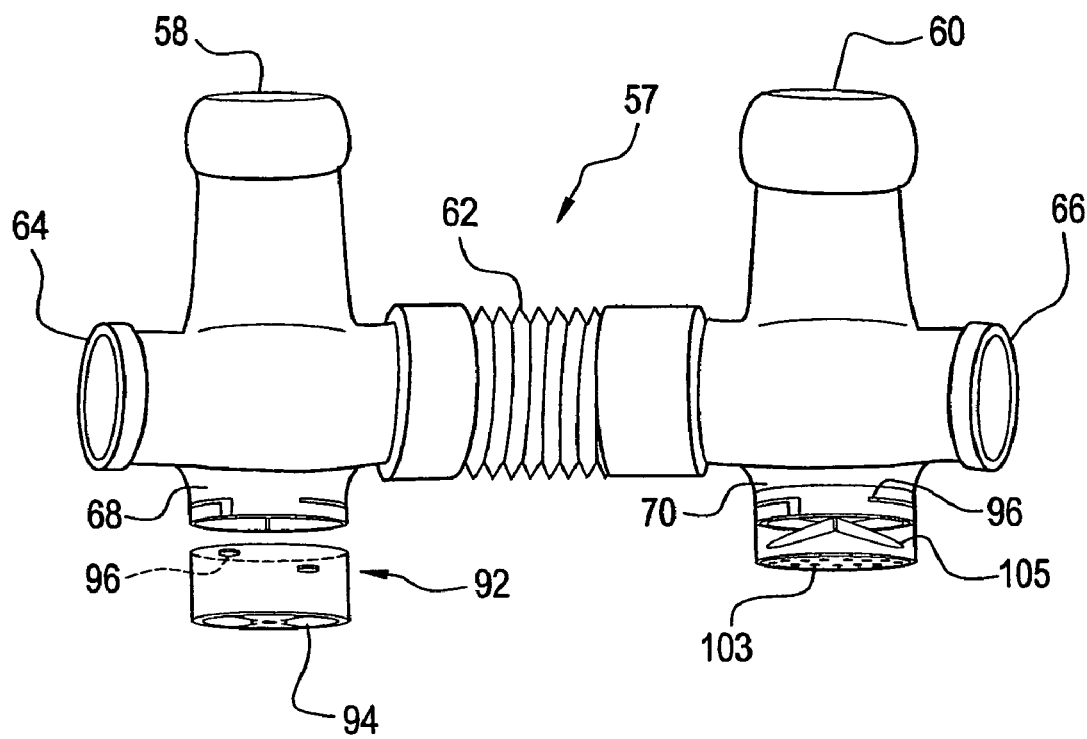
FIG. 9 shows an exemplary exploded view of the medicine delivery interface of FIG. 7 with adjustable flow restrictors.

FIG. 9 shows an exemplary exploded view of the medicine delivery interface with adjustable flow restrictors 92. FIG. 9 shows expiration ports 68, 70 disposed on the lower portion of intranasal device 57. The expiration ports 68, 70 may optionally be one-way valves configured to assist in cycling out exhaled gases and, additionally, prevent the ejection of the intranasal device 57 from the animal, for example, after sneezing. Alternatively, flow restrictors 92 may include a perforated disk 103 or vents 94 which may be connected to the expiration ports 68, 70 via a flange 96 or a retention ring (not shown). Alternatively, as another non-limiting example, the interface 4 may have an integrated adjustable aperture in the expiration ports 68, 70 which may be configured to control the outflow resistance. Alternatively, a separable device such as an adjustable flow restrictor 92 may be connected to the interface 4 by deformation, clamping or any other connection means known by a person having ordinary skill in the art.

In yet another non-limiting example, FIG. 9 shows expiration ports 68, 70 disposed on the lower portion of intranasal device 57. The expiration ports 68, 70 may optionally be one-way valves configured to assist in cycling out exhaled gases and, additionally, prevent the ejection of the intranasal device 57 from the animal, for example, after sneezing. Alternatively, flow restrictors 92 may include a perforated disk 103 and flexible membrane 105 which may be connected to the expiration ports 68, 70 via a flange 96 or a retention ring (not shown). When in a closed position, flexible membrane 105 is in connection with cross member and tension ring 78, thus creating a seal and preventing inward air or any other fluid movement.

Figure 10A:
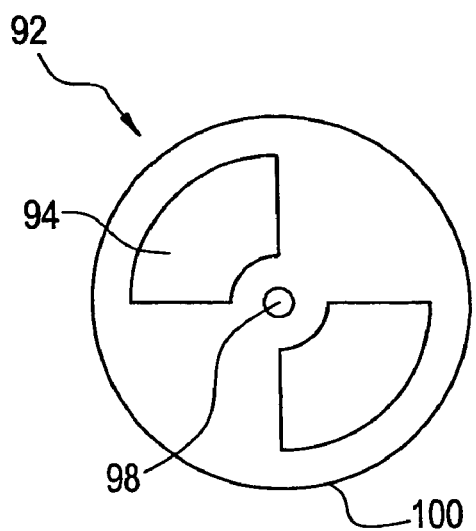
FIG. 10A shows a bottom view exemplary embodiment of an adjustable flow restrictor in an open position.

FIG. 10A shows an exemplary bottom view of an adjustable flow restrictor 92, with an out edge 100 and vents 94 positioned in the open position. The flow restrictor 92 may, alternatively, be placed in close proximity to the exhalation ports 68, 70 to control pressure within the interface.

Figure 10B:
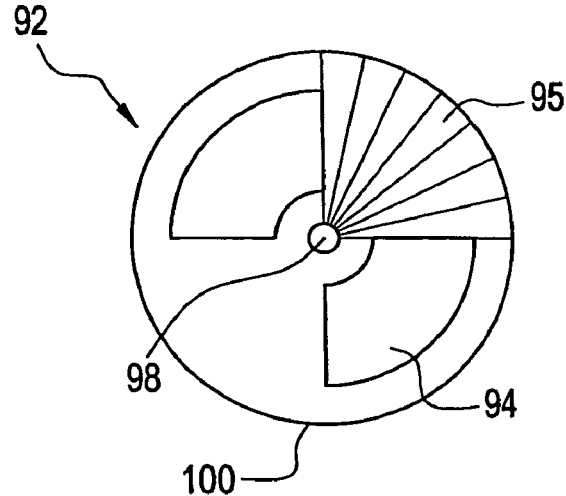
FIG. 10B shows a bottom view exemplary embodiment of an adjustable flow restrictor in a partially open position.

FIG. 10B shows another exemplary bottom view exemplary embodiment of an adjustable flow restrictor 92 with an outer edge 100 in a partially open position including a flow adjustment flange 95 which may be connected to a center 98 of the adjustable flow restrictor 92. The flow adjustment flange 95 may slide along the surface of the flow restrictor 92 to open or close the vent 94 to achieve the desired flow rate. Similarly, at least one of the flow restrictors 92 may have markings to designate desired flow rate. The adjustable flow restrictor 92 may be made in many forms with various vent 94 sizes, shapes and configurations known to one having ordinary skill in the art. For example, the adjustable flow restrictor 92 may be integrated with the interface or separable from the interface.

Figure 10C:
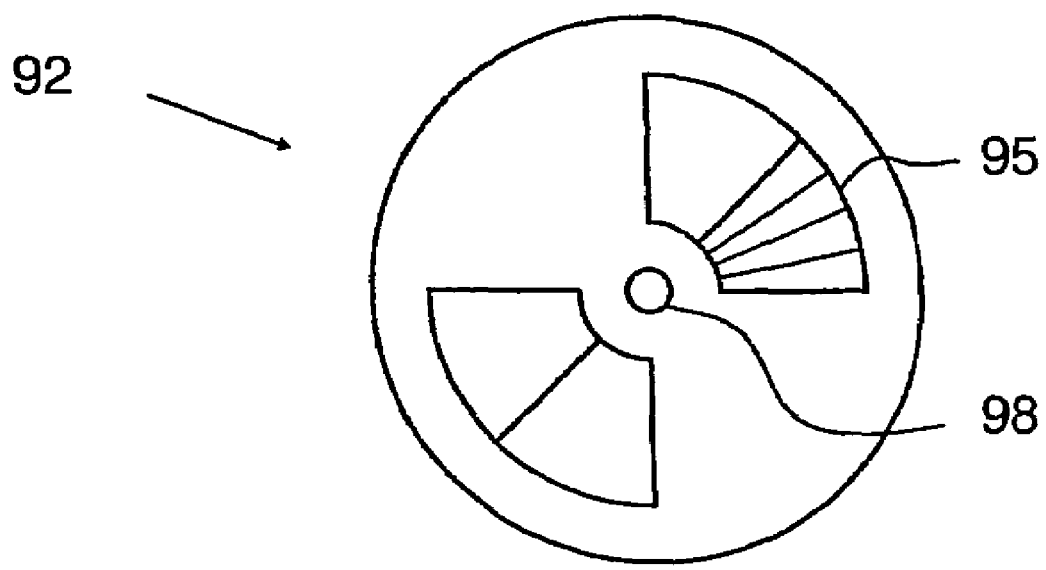
FIG. 10C shows another bottom view exemplary embodiment of an adjustable flow restrictor in a half open position.

FIG. 10C shows another exemplary bottom view exemplary embodiment of an adjustable flow restrictor 92 in a partially open position including a flow adjustment flange 95 which may be connected to a center 98 of the adjustable flow restrictor 92. The flow adjustment flange 95 may slide along the surface of the flow restrictor 92 to open or close the vent 94 to achieve the desired flow rate. In FIG. 10C the adjustable flow restrictor 92 is shown in the half open position. Similarly, at least one of the flow restrictors 92 may have markings to designate desired flow rate. The adjustable flow restrictor 92 may be made in many forms with various vent 94 sizes, shapes and configurations known to one having ordinary skill in the art. For example, the adjustable flow restrictor 92 may be integrated with the interface or separable from the interface.

Figure 10D:
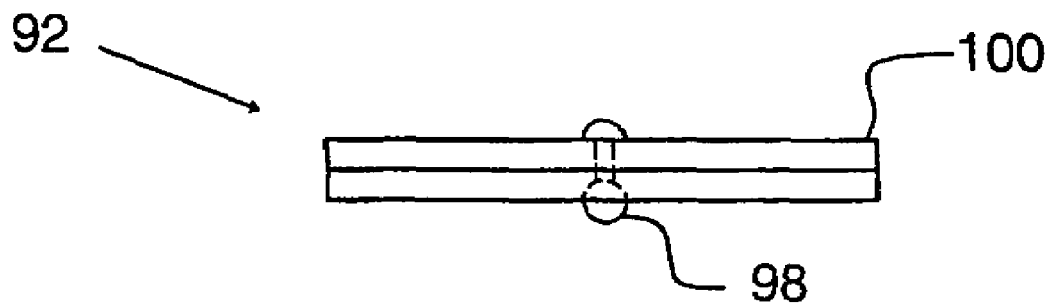
FIG. 10D shows a side view embodiment of an adjustable flow restrictor.

FIG. 10D shows an exemplary side view exemplary embodiment of an adjustable flow restrictor 92 with an outer edge 100 and with a center 98.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. An interface for delivery of therapeutic aerosols or gases, comprising:
  a plurality of hollow bodies having at least one nasal aperture defined therein and an exhaust flange extending away from each hollow body;

at least one nasal insert tube associated with the at least one nasal aperture of each hollow body is capable of being inserted into a nostril;
at least one exhaust aperture defined on each hollow body and in flow communication with the exhaust flange, the at least one exhaust aperture is configured to exhaust exhaled gases through the exhaust flange;
at least one exhaust valve coupled to the exhaust flange;
at least one flow restrictor coupled to the exhaust flange; and
at least one intake aperture.

2. The interface in claim 1, wherein the at least one exhaust aperture has at least one exhaust valve configured to exhaust exhaled gases and configured to block inflow of air through the exhaust aperture.

3. The interface of claim 2 further comprising a flange on the nasal insert tube configured to form a seal.

4. The interface of claim 2 further comprising a skirt on the nasal insert tube configured to form a seal.

5. The interface in claim 1, wherein each nasal insert tube is configured to form a seal with the nostril.

6. The interface in claim 1, wherein the at least one exhaust valve is a one-way valve.

7. The interface of claim 1, wherein the at least one intake aperture includes a one-way valve, wherein the one-way valve is capable of preventing air from passing through said intake aperture upon exhalation and wherein the one-way valve is capable of allowing air, therapeutic mists, vapors, aerosols or gases to pass through said intake aperture.

8. The interface of claim 1, further comprising two hollow bodies each having one nasal aperture, wherein the two hollow bodies are connected to one another but do not communicate with each other.

9. The interface of claim 1, further comprising two hollow bodies each with one nasal aperture, wherein the two hollow bodies are connected to one another and communicate with each other by way of a hollow tube body.

10. The interface of claim 1, wherein the at least one intake aperture is coupled to a reservoir configured to dispense therapeutic mists, vapors, aerosols or gases.

11. The interface of claim 1, wherein at least one of a nebulizer, vapor generator and inhaled therapeutic substance delivery device is disposed in close proximity to the intake aperture.

12. The interface of claim 1, further comprising:
a filter proximate to the intake aperture.

13. The interface of claim 1, further comprising:
a port configured to allow at least one of therapeutic mists, vapors, aerosols and gases to be delivered to the nasal interface.

14. The interface of claim 1, wherein the least one intake aperture is coupled by tubing to a nebulizer.

15. The interface of claim 1, wherein the at least one flow restrictor is adjustable.

16. A method for delivery of therapeutic aerosols or gases, comprising:
providing a plurality of hollow bodies having at least one nasal aperture defined therein, at least one exhaust flange extending away from each hollow body and at least one exhaust aperture defined on each hollow body and in flow communication with the at least one exhaust flange, wherein the at least one flange includes at least one exhaust valve and at least one flow restrictor coupled thereto;
inserting at least one nasal insert tube associated with each nasal aperture of each hollow body into a nostril;
delivering at least one of therapeutic mists, vapors, aerosols and gases to a nasal interface; and
expelling exhaled air through at least one of the exhaust valve and flow restrictor of each exhaust aperture.

17. The method of claim 16 wherein the inserting step the at least one nasal tube further comprises:
sealing each nasal insert tube configured to form a seal with the nostril.

18. The method of claim 16, further comprising:
expiring air through at least one exhaust valve which is a one-way valve.

19. The method of claim 16, wherein delivering at least one of therapeutic mists, vapors, aerosols and gases to the nasal interface further comprises:
preventing air from passing through said intake aperture upon said expelling of exhaled air and wherein a one-way valve is capable of allowing air, therapeutic mists, vapors, aerosols or gases to pass through said intake aperture.

20. The method of claim 16, wherein providing the plurality of hollow bodies further comprises:
providing two interfaces each having one nasal aperture, wherein the two interfaces are connected to one another but do not communicate airflow with each other.

21. The method of claim 16, wherein providing the plurality of hollow bodies further comprises:
providing two interfaces each with one nasal aperture, wherein the two interfaces connect to one another and communicate with each other by way of a hollow body.

22. The method of claim 16, further comprising:
connecting the at least one intake aperture to a reservoir configured to dispense at least one of therapeutic mists, vapors, aerosols or gases.

23. The method of claim 16, further comprising:
providing at least one of a nebulizer, vapor generator and inhaled therapeutic substance delivery device which is disposed in close proximity to the intake aperture and operably coupled to provide therapeutic delivery.

24. The method of claim 16, further comprising:
filtering the therapeutic air prior to delivery to the intake aperture.

25. The method of claim 16, wherein the expelled air is at least one of therapeutic mists, vapors, aerosols and gases.

26. An interface for delivery of therapeutic aerosols or gases, comprising:
means for delivery of aerosols through at least one hollow body having at least one nasal aperture defined therein;
means for sealing at least one nasal insert tube configured to form a seal with a nostril, wherein the at least one nasal insert tube is associated with each nasal aperture of said hollow body;
means for exhausting exhaled gas;
means for blocking inflow of air through the means for exhausting exhaled gas;
means for restricting flow of exhaled gas through the means for exhausting exhaled gas: and
means for intake of at least one of therapeutic aerosol or gases;
at least one exhaust aperture defined on each hollow body and in flow communication with an exhaust flange, the at least one exhaust aperture is configured to exhaust exhaled gases through the exhaust flange; at least one exhaust valve coupled to the exhaust flange; at least one flow restrictor coupled to the exhaust flange; and at least one intake aperture.

27. An interface for delivery of therapeutic aerosols or gases, comprising:

at least one hollow body having at least one nasal aperture defined therein;

at least one nasal insert tube associated with the at least one nasal aperture of said hollow body is capable of being inserted into a nostril;

at least one integrated adjustable exhaust aperture defined on each hollow body and in flow communication with an exhaust flange, the at least one exhaust aperture is configured to exhaust exhaled gases through the exhaust flange; at least one adjustable exhaust valve comprising flexible membranes configured to exhaust exhaled gases and configured to prevent inhalation of air through the /exhaust aperture coupled to the exhaust flange; at least one flow restrictor coupled to the exhaust flange; and at least one intake aperture.

28. An adjustable flow restrictor for delivery of therapeutic aerosols or gases comprising:

a cylindrical body, at least one connection flange on the cylindrical body, and at least one vent, wherein the flow restrictor is coupled to an interface comprising:

at least one hollow body having at least one nasal aperture defined therein;

at least one nasal insert tube associated with the at least one nasal aperture of the hollow body is capable of being inserted into a nostril;

at least one exhaust aperture defined on each hollow body and in flow communication with an exhaust flange, the at least one exhaust aperture is configured to exhaust exhaled gases through the exhaust flange; at least one exhaust valve coupled to the exhaust flange; at least one flow restrictor coupled to the exhaust flange; and at least one intake aperture.

29. The interface in claim 28, further comprising:

a flow adjustment flange connected to the cylindrical body.

30. The interface in claim 28, wherein the at least one vent is substantially rectangular.

31. The interface in claim 28, wherein the at least one vent is substantially circular.

* * * * *